United States Patent
Boender et al.

(10) Patent No.: US 10,085,857 B2
(45) Date of Patent: Oct. 2, 2018

(54) HYDRAULIC PROSTHETIC JOINT

(71) Applicants: Jacob Quintus Laurence Anthony Boender, Marcham (GB); Jona Aelrid Brendan Boender, Marcham (GB)

(72) Inventors: Jacob Quintus Laurence Anthony Boender, Marcham (GB); Jona Aelrid Brendan Boender, Marcham (GB)

( * ) Notice: Subject to any disclaimer, the term of this patent is extended or adjusted under 35 U.S.C. 154(b) by 3 days.

(21) Appl. No.: 15/045,217

(22) Filed: Feb. 16, 2016

(65) Prior Publication Data
US 2016/0235558 A1 Aug. 18, 2016

(30) Foreign Application Priority Data
Feb. 13, 2015 (GB) .................................. 1502504.2

(51) Int. Cl.
| | |
|---|---|
| *A61F 2/74* | (2006.01) |
| *A61F 2/64* | (2006.01) |
| *A61F 2/60* | (2006.01) |
| *A61F 2/68* | (2006.01) |
| *F16F 9/512* | (2006.01) |

(Continued)

(52) U.S. Cl.
CPC ................ *A61F 2/604* (2013.01); *A61F 2/64* (2013.01); *A61F 2/68* (2013.01); *F16F 9/5126* (2013.01); *A61F 2002/5004* (2013.01); *A61F 2002/5006* (2013.01); *A61F 2002/5033* (2013.01); *A61F 2002/5035* (2013.01); *A61F 2002/6863* (2013.01); *A61F 2002/704* (2013.01); *A61F 2002/74* (2013.01); *A61F 2002/745* (2013.01);

(Continued)

(58) Field of Classification Search
CPC ...... A61F 2002/5003; A61F 2002/5004; A61F 2002/5006; A61F 2002/5033; A61F 2002/5035; A61F 2002/745; A61F 2002/748
See application file for complete search history.

(56) References Cited

U.S. PATENT DOCUMENTS

| | | | |
|---|---|---|---|
| 2,561,370 A * | 7/1951 | Henschke | ................. A61F 2/64 623/26 |
| 5,376,137 A | 12/1994 | Shorter et al. | |

(Continued)

FOREIGN PATENT DOCUMENTS

GB 779087 A 7/1957

*Primary Examiner* — David H Willse
(74) *Attorney, Agent, or Firm* — Galvin Patent Law LLC; Brian R. Galvin

(57) ABSTRACT

The present invention relates to artificial limbs generally and to joints for the same. In particular, the present invention provides hydraulic functional units, generally classified as damping devices as connected between artificial limbs whereby enabling movement of artificial joints to closely correspond with natural human movement. In accordance with the invention, there is provided hydraulic damper control elements for prostheses which utilize a pressure differential due fluid flow as a direct control input for a at least one hydraulic valve. The valve can comprise a moveable element which abuts a mounted element which reduces the size of an aperture as the force increases. Further, a moveable body acts upon the valve enabling increase or decrease of flow of hydraulic fluid through the valve, whereby enabling an increase in gait by way of reduction of resistance to flow or reducing or stopping flow by way of a stumble recovery mechanism.

19 Claims, 9 Drawing Sheets

(51) Int. Cl.
    *A61F 2/50*         (2006.01)
    *A61F 2/70*         (2006.01)
    *A61F 2/76*         (2006.01)

(52) U.S. Cl.
    CPC . *A61F 2002/748* (2013.01); *A61F 2002/7655* (2013.01)

(56) References Cited

U.S. PATENT DOCUMENTS

| | | |
|---|---|---|
| 6,106,560 A | 8/2000 | Boender |
| 8,915,969 B2 | 12/2014 | Boender |
| 2007/0208431 A1 | 9/2007 | Bisinger et al. |
| 2011/0307078 A1* | 12/2011 | Boender ................ A61F 2/605 623/26 |

* cited by examiner

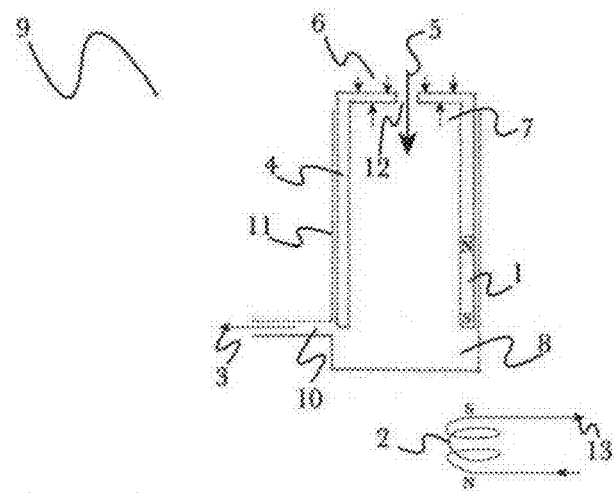
Fig. 4'
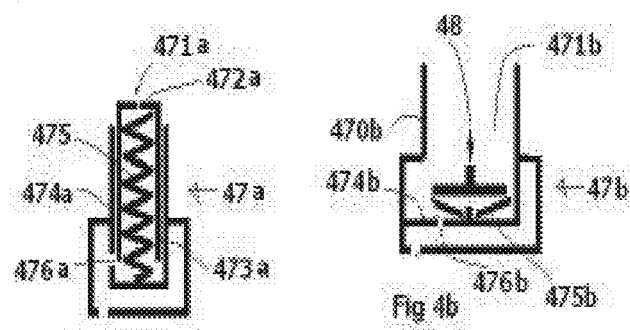
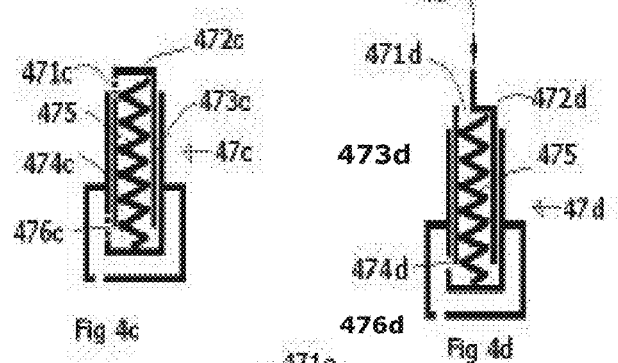
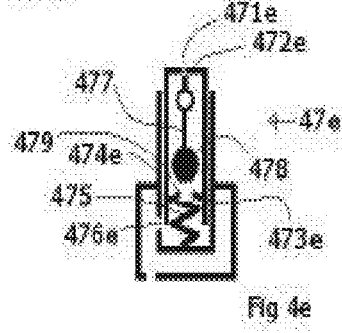

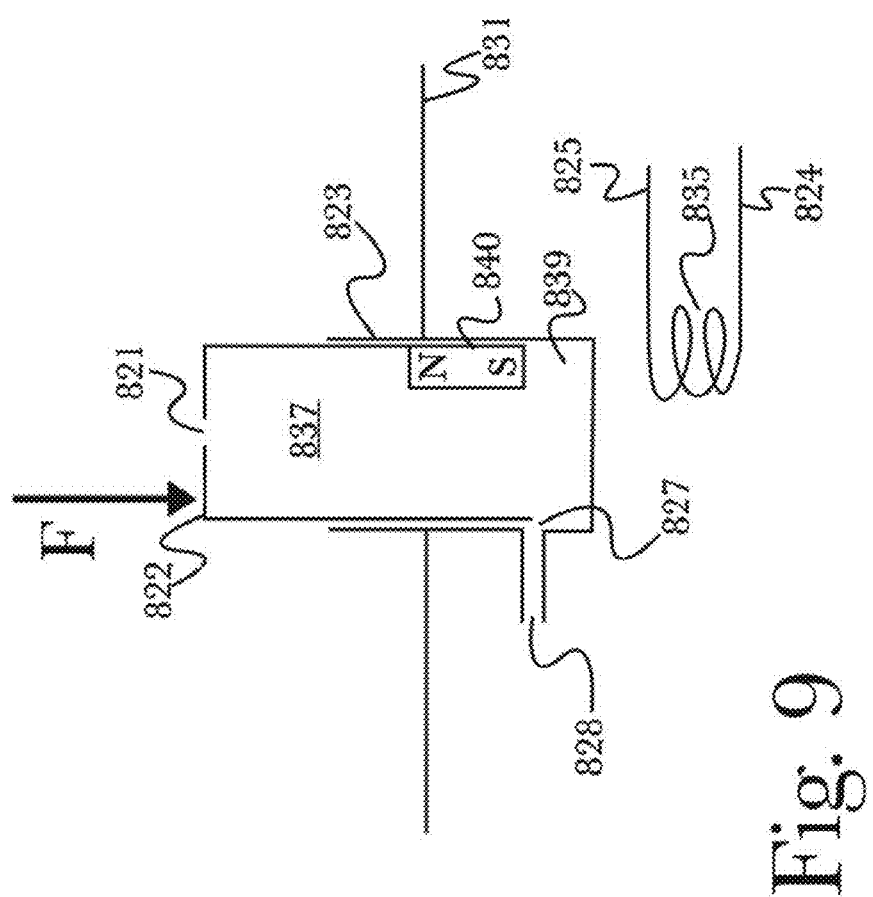

HYDRAULIC PROSTHETIC JOINT

CROSS-REFERENCE TO RELATED APPLICATIONS

This application is a continuation of UK patent application serial number GB 1502504.2, titled, "A HYDRAULIC PROSTHETIC JOINT", which was filed on Feb. 13, 2015, the entire specification of which is incorporated herewith by reference in its entirety.

BACKGROUND OF THE INVENTION

Field of the Art

The present invention relates to artificial limbs generally and to joints for the same. In particular, the present invention provides hydraulic functional units, generally classified as damping devices as connected between artificial limbs whereby to enable movement of artificial joints to closely correspond with natural human movement.

Discussion of the State of the Art

In the provision of realistic joints, as used in prosthetic limbs, an important aspect in attempting to achieve a realistic movement is to provide a different operating characteristic to the joint when under load. Indeed, one of the more important characteristics of an artificial leg for achieving a natural-looking walking gait correspond with those of a so called stabilized knee, i.e. a knee which resists flexion when under load, that is when it is bearing at least some of the weight of the amputee. It can be said that the test is somewhat subjective if one were to view an amputee with an artificial leg, but mere observation is one of the best tests; a strange gait is generally immediately apparent; this can cause unwelcome stares to amputees, who when fitted with a pair of long trousers would otherwise not be noticed when in a crowd.

Early prosthetic limb systems, dating from the 1950's were provided with friction brake devices. For example, in GB779087, when utilized in a knee joint application, there was a provided a shin and knee joint mechanism which included a drum fixed to the shin, with one or more bands connected to the thigh and embracing the drum so that the bands gripped the drum to lock the knee when the leg was bearing weight, actuating means associated with the shin and thigh operated to release the lock just before the foot left the ground in walking, with a connection between the shin and thigh permitting relative axial movement between the shin and thigh. In this device, however, an axial load on the limb produced a small rotation of the radius arm or arms causing the brake band or brake shoe to grip the drum and to resist knee flexion. Indeed, the resistance would frequently become so great such that the knee became automatically locked once sufficient load had been applied. Later devices were combined with a pneumatic piston and cylinder assembly, which applied lower degrees of resistance to flexion and/or extension of the knee to control the motion of the shin during the swing phase.

In recent years, however, such friction-based systems—which required regular servicing and adjustment—have been replaced by hydraulic dampers with external control, which provide resistance to flexion during a stance phase as well as a swing phase of operation by means of a piston and cylinder assembly. Hydraulic artificial knees provide stability to the prosthesis when the patient's weight is borne on the prosthesis, and collapse must be prevented. To prevent collapse of a free artificial knee joint the joint must receive appropriate information to inform it of its required mode of function. The hydraulic knee joint operates by utilizing a volume of incompressible fluid to the knee joint, whereby to provide mechanical stability.

One example of such an arrangement is the hydraulic "S-N-S" knee control system manufactured by Mauch Laboratories, Inc. In some situations, however, this system required an amputee to make a knee-extending movement before flexion could be initiated. Additional problems arose through external wear and through the fact that they require actuation, which is, of course dependent upon movement being regular. As is known, when walking, one will vary one's gait to go down stairs, to cross steps, to avoid obstructions and the like. In some cases mechanical switching of the valve will not be effected properly. U.S. Pat. No. 5,376,137 to Blatchford is an example of a weight activated knee joint with hydraulic amplification of weight application triggered pivotal movement, whilst U.S. Pat. No. 6,106,560 to Ultimate Knee teaches of a weight activated knee joint with mechanical amplification of weight application triggered pivotal movement. US20070208431 (Bisinger) provides a pneumatic swing phase control device having a piston-cylinder device defining a wall between first and second chambers; first and second throttles are provided for controlling aspiration into and exhaust from said chambers and to close when a predetermined pressure has been reached.

While recent hydraulic devices are believed to be much improved they are complex and costly to manufacture since they are manufactured to high tolerances. On the one hand, if mechanical external valve control is provided, then there will be problems as discussed above; on the other hand, electronic flow control valves can be provided—that are expensive to purchase and maintain—which enable amputees to walk with a pre-determined gait yet will not necessarily be reactive to uneven surfaces.

To assist in the understanding of the problems addressed by the present invention, reference can be made to standard testing techniques, as employed to assess the fitness of an amputee to walk with or without assistance. FIG. 1 is a graph that represents the maximum knee flexion angle in swing at various walking speeds for three known devices of prosthetic knee joints, (Source: "What are the benefits of the C-Leg?" (J. Kastner, R. Immervoll, H. Kristen & P. Wagner)). The graph shows a clear change of at least 10° in angular variation of knee flexion movement as an increase in walking speed for the computer controlled device yet a change of 20° over a speed change of 2 km/h for a known mechanically controlled device. The plot of knee flexion for a normal gait; i.e., for a person with the full use of their own limbs is shown for comparative purposes. It can be seen that the variation in knee flexion angle is more or less absent, for a control person, with full use of their own legs, despite an increase in speed to approximately double that of the initial speed. In simple terms, to the casual observer, the person wearing such artificial limbs would be seen to have an ungainly gait due to a delay in knee extension needed to prepare the limb for weight acceptance. In another study "User-adaptive control of a magneto-rheological prosthetic knee" (H. Herr and A. Wilkenfeld) which appeared in Industrial Robot: An International Journal Volume 30, Number 1, 2003, 42-55, where a computer controlled prosthesis—a Rheo Knee—was tested. A horizontal response was produced but the study was limited to below 5 km/hr limit, which is less than normal walking speeds.

Certain prostheses provide joints that use a weight activated safety mechanism which is energized by forces arising from the user's weight bearing on the artificial limb, that can be detected and be made effective in implementing a change in resistance to limb pivoting. Such a movement can be the compression of one of the members that form a mechanical chain from the amputation stump to the ground, and which can be detected by strain gauges, by small amounts of telescopic deformations, or limited ranges of pivotal movements such as the knee or ankle and can typically be detected as relative displacements of two suitably chosen points. The pivotal movements can be amplified mechanically (including hydraulically) or electronically and/or can be made to be more sensitive to forces transmitted through a heel of an artificial foot as opposed to those input through a fore part of a foot.

Problems arising from the use of weight activated knee joint control mechanisms include the fact that the residual weight taken by the artificial limb on toe-off can inhibit a release of the weight-activated mechanism. Typically an apparatus or means is supplied to cause a threshold value of weight required to activate the knee stability. Whilst this threshold is easily overcome by forces passing through the heel, the threshold is not easily overcome by forces passing through the toe. Nevertheless, this threshold reduces the chance of unintentional activation on heel strike, but means that some attention needs to be paid as to how one walks with such a prosthesis at all times. This threshold also makes it difficult to maintain stability of the knee, when extension after mid swing is incomplete the respective foot is susceptible of hitting the ground too early. This is particularly true when traversing rough pathways. Typically the weight-activation class of knee joints do not provide security against collapse in such conditions or in the event of accidental use.

One difficulty to be overcome by users of prosthetic lower limbs is that it is counter intuitive to place one's body weight onto the device to secure the same body weight against sudden collapse. This is not a problem in certain types of knee, which default to a weight acceptance mode; the knee stability is deactivated by a mechanism that detects hyperextension of the knee joint, which typically goes together with a load on a forefoot part of the prosthesis, but which can also be provided by voluntary hip femoral stump hip extension. Again there is a small movement that can inform the knee design of a required change of status, and also here various similar signal amplification means can be employed, i.e. mechanical, electronic, hydraulic etc. . . .

Whereas the weight activated mechanisms have their weight application input parameter present throughout an activation period, the hyperextension that deactivates the knee stability mode is removed as soon as the joint commences its permitted free flexion to support the required free knee flexion for swing, as required in the use of a free knee, which requires the joint to have a memory, for a period as long as the knee is in free flexion mode, being a preceding condition of hyperextension. This period corresponds to the first half of the pendulum swing movement of the shank of the prosthesis relative to the thigh member. Additionally, the memory mode must be deactivated on knee extension in order to return the knee joint to its default state, where it must be ready to take an amputee's weight.

FIG. 2 details a switching function of the Mauch SNS prosthesis, wherein the memory function is determined by a mechanical arrangement (as opposed to an electronic timer arrangement, for example). Specifically, the memory comprises an eccentric toggle ($H_1$), that resumes a gravitationally neutral position unless prevented by an open state of a valve member ($H_3$), which is energized by hydraulic pressure ($H_4$) caused by a flex movement of the free knee. It is notable that this linkage is not instantaneous; release of the memory function takes a time frame independent of the time it takes to reapply weight on the prosthesis. In the event of an inadvertent early reapplication of weight on the prosthesis, the toggle would likely not be in a position to allow closure of the valve, which could be painful and perhaps cause an amputee to fall over following knee collapse in such circumstances. In effect, the memory of this prior teaching is continued for a longer period than desired whereby to cause at the very least a non-natural gait, with an increased likelihood of a fall occurring due to the time required for a change in state being far greater than desirable. This is referred to as a stumble recovery problem.

In addition to the abovementioned stumble problem, another issue of note is that when a prosthetic lower limb is correctly fitted, it will tend to be fitted to provide appropriate levels of resistance to movement whilst the amputee is walking at what is a comfortable pace. Any increase in speed results in a burden arising from the damper settings providing too much resistance if the amputee wishes to go faster or, indeed, does not provide sufficient resistance at a speed at a normal rate. Whilst this may apparently appear to be great, it will be appreciated that a user of a prosthetic limb will want to not match their speed with friends who may not realize that a person with a prosthetic limb has an optimum speed. In U.S. Pat. No. 8,915,969, Boender teaches of a fluidic valve operable to control the movement of a prosthetic joint. The fluidic valve is controlled by three elements: a moveable part to dynamically occlude an exit aperture of the valve, a metering entry aperture to the valve and a resilient member disposed between these apertures. Derivative valves are also disclosed, where the inlet or entry aperture can be varied in accordance to say, a position of a piston within such a damper, by position of the moveable part the entry aperture or even by gravity. A perceived shortcoming in this approach is that the metering aperture is not easily controlled in an on-demand fashion, with the functionality of the valve is necessarily determined as a function of fluid flow and positions of associated elements of the damper arrangement.

The present invention seeks to overcome or ameliorate at least some of the disadvantages described above. It is a further object of the invention to seek to utilize the fluid properties of the working fluids and the architectures of the ducts and passages to enable a hydraulic damper arrangement that can vary levels of movement damping resistance in an adaptive fashion to user operation. Notwithstanding this, it is a further object of the invention to permit alternative embodiments to prosthetic joints controlled by a damper and to enable alternative/additional control. Another object of the invention to provide a leg prosthesis that enables a more immediate release of a memory function, but remain sensitive to a required completion of the knee flexion movement in the first half of the swing phase, when required as is the case across uneven terrain.

SUMMARY OF THE INVENTION

Accordingly, the inventor has conceived and reduced to practice, in a preferred embodiment of the invention, a hydraulic prosthetic joint to address the aforementioned problems.

In accordance with the present invention, there is provided a prosthesis in accordance with the features of claim 1. The prosthesis, under normal conditions has a hydraulic damper wherein a fluid flow rate of the incompressible hydraulic fluid through the valve is a conditioned function of a second pressure, which second pressure is less than the first pressure and is associated with fluid flow through the valve and is operable to maintain a positive flow rate through the valve as the first pressure increases, the conditioned function being determined such that the second pressure as a function of the flow rate causes an increase in resistance of the valve to the flow caused by the first pressure, such that the fluid flow approaches but does not reach a maximum as the first pressure increases past a minimum pressure, whereby a fluid flow limit is established through the valve. A sensor to flow and or pressure is therefore also provided, which sensor conveniently enables control of an additional control element, for example under the control of a magnetic field, to enable control of a moveable body which acts upon the valve to enable an increase or decrease of flow of hydraulic fluid through the valve. Piezoelectric, magnetic, electromagnetic, and/or electrical signals can otherwise or additionally be employed in the provision of this sensor. Control of flow about or through a valve flow control element can conveniently be determined by one of a microprocessor, analogue or electrical switched circuits. That is to say, the sensor can cause an additional control element to operate whereby, where the limb is a leg, to enable an increase in gait by way of reduction of resistance to flow or to reduce or stop flow by way of a stumble recovery mechanism. The device can comprise a rotary or oscillatory sensor, whereby to create an electrical pulse or wave that carries information about the state of flow and change in rate of flow. This electrical signal can then be separated in information and now redundant energy. This energy can then be re-modulated via a microprocessor into a signal to drive an electro-fluidic valve or electro-fluidic transistor. A small current passing through the coil of the valve device alters the tension on the movable valve body as to act as the regulator of the flow rate, independent of main driving pressure as known from the prior art. In the limit, upon a reversal of current through a valve coil can cause closure of a valve, a function neither disclosed nor suggested in the prior art. The present invention can therefore provide a controllable variable force that can more rapidly alter the properties of the valve.

By the provision of a hybrid construction in having both a mechanical resilient member as well as a piezoelectric, electromagnetic, electrostatic or magnetic force acting on the same moveable skirt of the valve can have advantages: the resilient member can take responsibility for the normal function of the valve, having a passively determined dynamic response of the knee joint as disclosed in, for example, U.S. Pat. No. 8,915,969, and therefore not requiring electrical power for total movement control, which electrical power needs to be provided by some power source, such as a battery of electrical storage cells, but with the added advantage of fine tuning control of the magnetic force or other known means of creating forces by electrical means such as electrostatics and piezoelectrics. The present invention can thus utilize an electrical measure of a rate of change of flexion as a source of system control upon a hydraulic valve, whereby to enable a variation in a pressure differential across a valve and thus to improve, in the case of a prosthetic leg, stumble recovery on the one hand and on the other hand to enable a variation in damping control to enable stability of use, irrespective of rate of a user's gait.

Thus, in a simple system, flow rate of a hydraulic fluid within a hydraulic damper as it flows back and forth between first and second reservoirs between a valve is monitored by means of a sensor, whereby, the rate of flow can be monitored so as to adapt a valve functionality; to increase the resistance in a stumble recovery mode for a prosthetic leg; to reduce the resistance as the speed of a continuous gait increases. The sensor can conveniently be arranged as a vane which moves in accordance with the direction of flow of fluid between the first and second reservoirs and, for example, becomes increasingly deflected the greater the speed of flow of fluid. In a first alternative a rotary paddle could be employed, such that the rotation of the paddle is measure of the degree of rate of change of fluid flow rate. Optionally, the sensor—or an additional sensor—can also provide data regarding joint position.

In the event that the flow stops instantaneously, then a stumble recovery mode could be instigated, causing fluid flow through a valve to be minimized or even prevented: instead of maintaining the valve in a controlled open state by preventing valve closure by magnetic force, a field reversal would instead force rapid valve closure. The vane could be connected to a microprocessor to determine when valve operation needs to be varied from a quiescent state. In the alternative a dc voltage could be generated which could be either employed directly to control a valve control mechanism or be amplified. The electricity output from a small generator is conveniently damped and stored using capacitors. An electromagnet or other positioning unit can be employed to alter the operating characteristics of a valve; from being fully closed in a stumble recovery mode to a condition of providing less resistance when an increase in gait is desired, the valve acting between two chambers of a damper can be further, additionally controlled.

The valve can comprise a moveable element which abuts a resiliently mounted element which reduces the size of an aperture as the force increases and acts against the resiliently mounted element the degree of resilience being varied, for example by a varying magnetic field, controlled by the operation of the sensors. A rheomagnetic fluid can be employed, whereby a magnetic field can determine the flow characteristics of the hydraulic fluid to be continuously controlled by a variable electromagnet under control of a microprocessor.

The present invention is particularly applicable for the prosthetic limb being a leg, with the first artificial limb component being an upper leg element and the second artificial limb component being a lower leg or a hip element, the joint pivotally coupling said first and second limb being a knee or hip joint. Nonetheless, the limb can be an arm with the first artificial limb component being an upper arm element and the second artificial component being a lower arm limb or shoulder element, the joint pivotally coupling said first and second limb being an elbow or shoulder joint. The prostheses in accordance with the present invention can comprise one of or both an artificial skeletal limb or a brace for hip, limb or ankle. Conveniently, the valve is adjustable to provide variable conditional control to the motion of said joint by permitting changes to its angular status. The fluid can be selected from one of a combination of the following fluids; a hydrocarbon based fluid, a silicone based fluid or rheomagnetic fluid.

In another aspect, the use of flow pressure differentials conditions a normally closed valve to remain open; in different modes of use of a joint this serves to provide data to the effective memory of the system, to keep a normally closed valve open, and optionally use these pressure differentials as a means to energize the memory. Further, the use of the reverse flow pressure conditions as present, for example in an extension of a knee joint, can provide data to the effective memory of the system, to return to a quiescent state, to lose any memory upon extension, and optionally use these reverse pressure differentials as a means to effect a change of memory content is a second part of this aspect of the invention.

BRIEF DESCRIPTION OF THE DRAWING FIGURES

The accompanying drawings illustrate several embodiments of the invention and, together with the description, serve to explain the principles of the invention according to the embodiments. It will be appreciated by one skilled in the art that the particular embodiments illustrated in the drawings are merely exemplary, and are not to be considered as limiting of the scope of the invention or the claims herein in any way.

FIG. 1 is a graph that represents the maximum knee flexion angle in swing at various walking speeds for prior art prosthetic knee joints.

FIG. 2 details a known prosthesis hydraulic switch.

Figure 4:
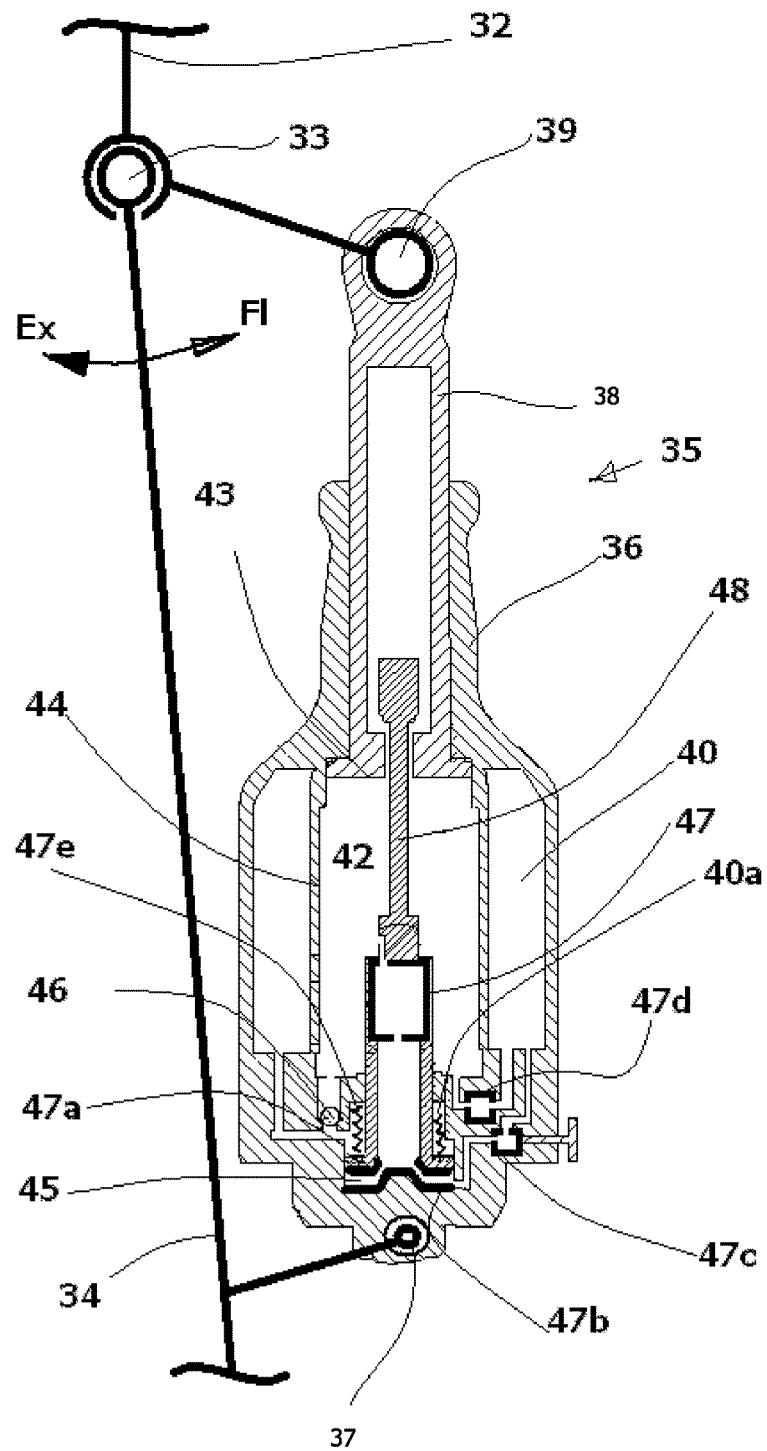
FIG. 4 is a cross-section through a generic device susceptible to modification by a control system in accordance with the present invention can be incorporated.

FIG. 4' is a cross-section through a first embodiment of a valve in accordance with the present invention.

FIGS. 4a-e detail valves operable with the present invention.

FIGS. 5a-e show different hydraulic dampers operable with the present invention.

Figure 6:
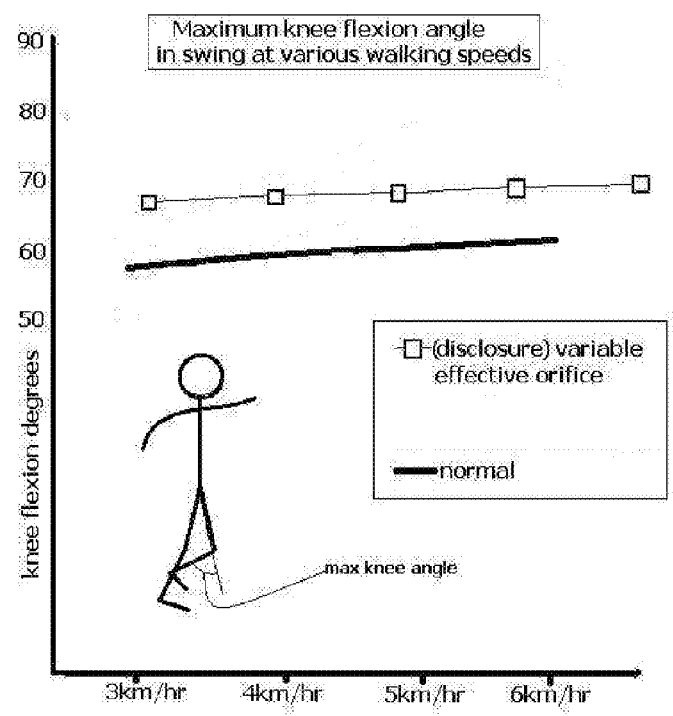

FIG. 6 is a graph that represents the maximum knee flexion angle in swing at various walking speeds for a knee joint of the invention.

Figure 7:
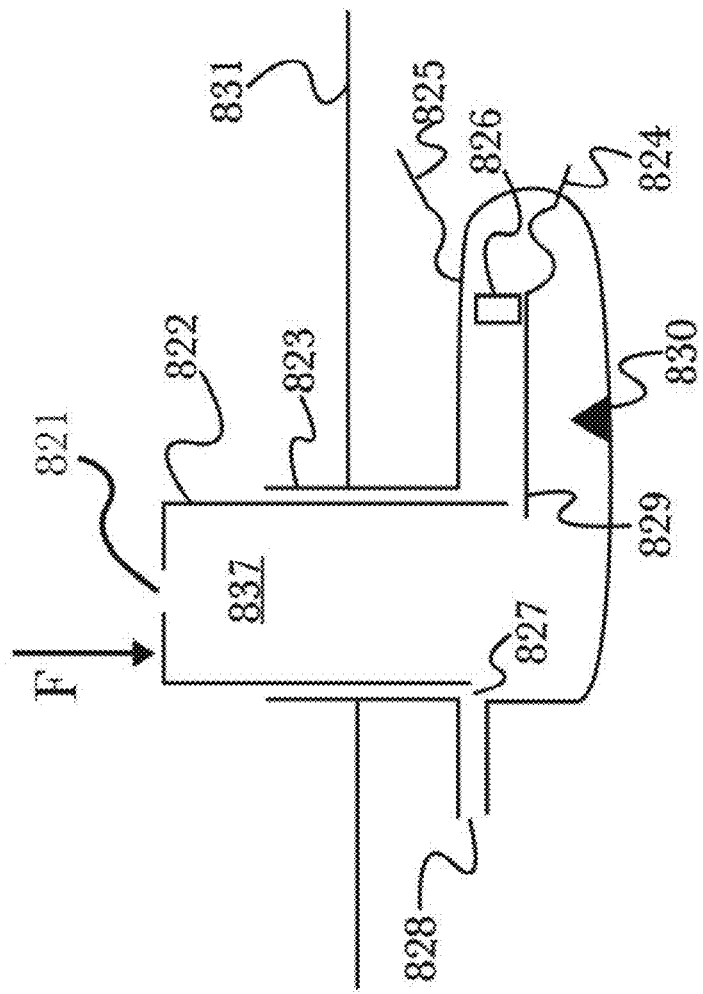
Figure 8:
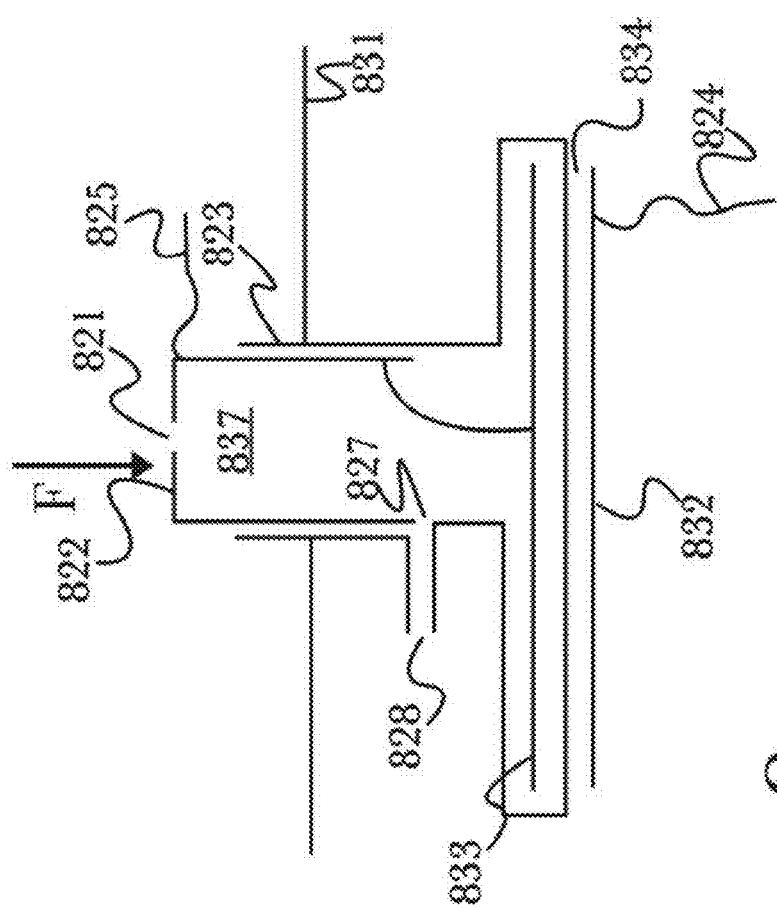

FIGS. 7-9 show three main conceptual embodiments of a valve made in accordance with the invention.

DETAILED DESCRIPTION

Definitions

The following terms have specific meanings and it is intended that reference shall be made to this lexicon in event of any doubt:

Brace: a support device to maintain a relative position of a limb with respect to the trunk or another limb; part of an external framework arranged about and intended to support limbs.

Hydraulic fluid: a substantially incompressible fluid operable in hydraulic lines, hydraulic rams and hydraulic systems.

Hydraulic damper: a hydraulic device comprising at least a first variable volume of hydraulic fluid, wherein the volume of hydraulic fluid retained within the hydraulic actuator is proportional to an amount of actuation associated with a joint to which the hydraulic damper is coupled.

Prosthesis: an artificial part such as an artificial limb; an artificial or mechanical aid such as a brace.

Prosthetic joint: an artificial joint associated with the repair or replacement of a skeletal joint; the term includes external orthopedic joints.

Orthopedic joint: a skeletal joint; a joint of the limbs; a joint such as the hips.

Valve: a device operable to regulate or control the flow of a fluid in a passageway, such as a pipe or duct, between two volumes; a device operable to regulate or control the flow of a fluid, but not necessarily preventing flow of said fluid.

DETAILED DESCRIPTION OF PREFERRED EMBODIMENTS

The inventor has conceived, and reduced to practice, in a preferred embodiment of the invention, a hydraulic prosthetic joint.

One or more different inventions may be described in the present application. Further, for one or more of the inventions described herein, numerous alternative embodiments may be described; it should be appreciated that these are presented for illustrative purposes only and are not limiting of the inventions contained herein or the claims presented herein in any way. One or more of the inventions may be widely applicable to numerous embodiments, as may be readily apparent from the disclosure. In general, embodiments are described in sufficient detail to enable those skilled in the art to practice one or more of the inventions, and it should be appreciated that other embodiments may be utilized and that structural, logical, software, electrical and other changes may be made without departing from the scope of the particular inventions. Accordingly, one skilled in the art will recognize that one or more of the inventions may be practiced with various modifications and alterations. Particular features of one or more of the inventions described herein may be described with reference to one or more particular embodiments or figures that form a part of the present disclosure, and in which are shown, by way of illustration, specific embodiments of one or more of the inventions. It should be appreciated, however, that such features are not limited to usage in the one or more particular embodiments or figures with reference to which they are described. The present disclosure is neither a literal description of all embodiments of one or more of the inventions nor a listing of features of one or more of the inventions that must be present in all embodiments.

Headings of sections provided in this patent application and the title of this patent application are for convenience only, and are not to be taken as limiting the disclosure in any way.

The functionality or the features of a device may be alternatively embodied by one or more other devices that are not explicitly described as having such functionality or features. Thus, other embodiments of one or more of the inventions need not include the device itself.

There will now be described, by way of example only, the best mode contemplated by the inventor for carrying out the present invention. In the following description, numerous specific details are set out in order to provide a complete understanding to the present invention. It will be apparent to those skilled in the art, that the present invention may be put into practice with variations of the specific.

Figure 1:
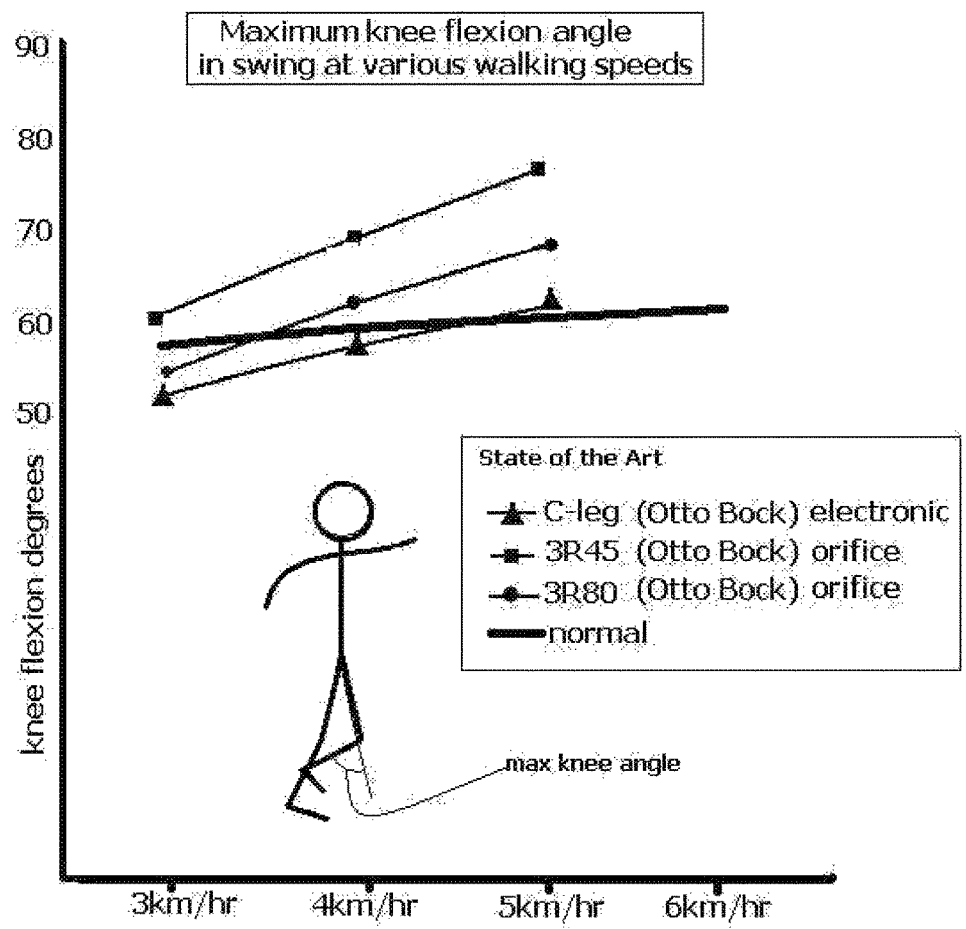
Figure 2:
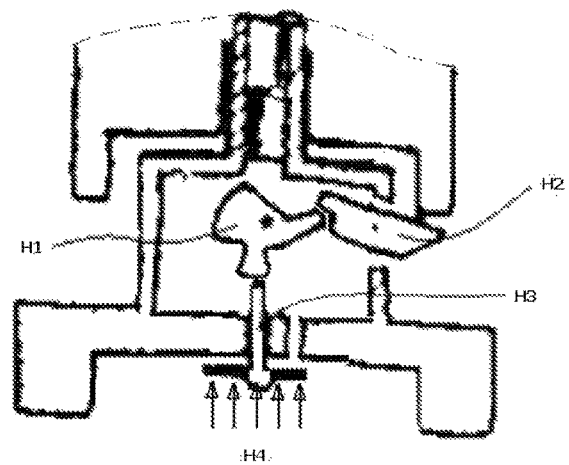
Figure 3:
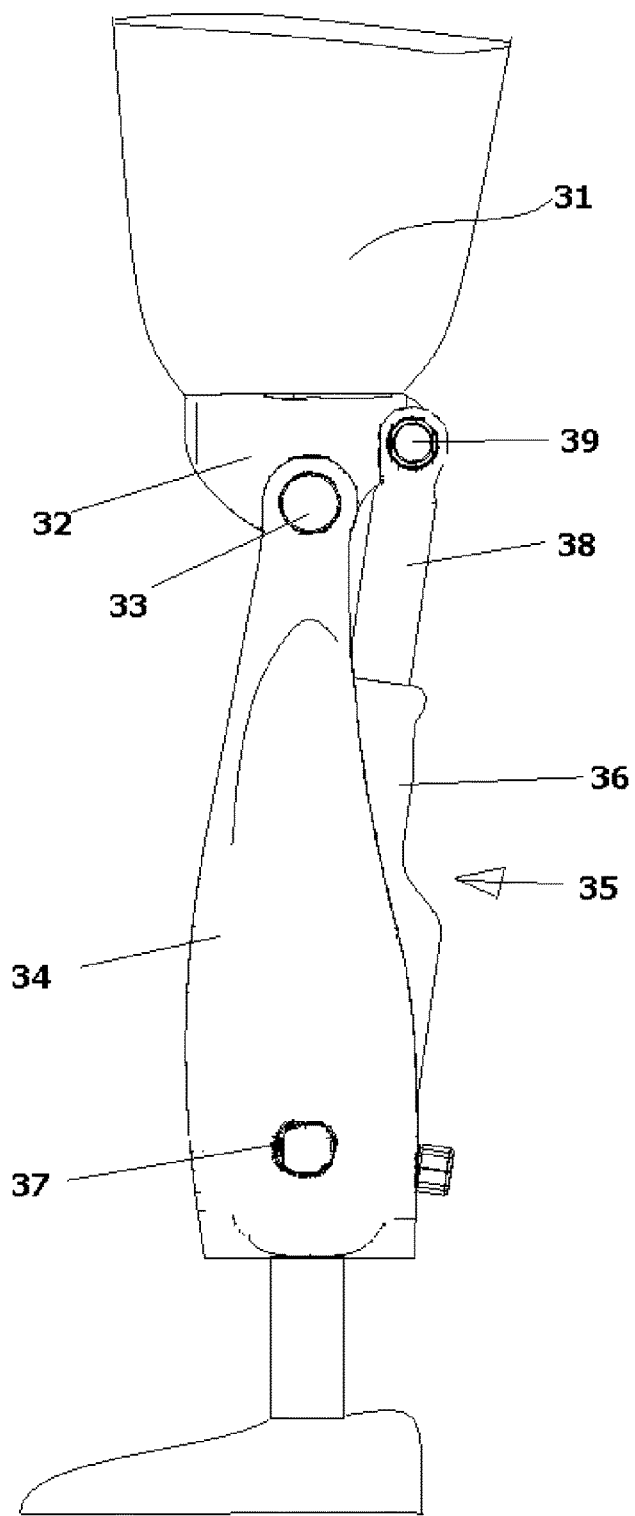
FIG. 3 shows a leg prosthesis with a hydraulic damper.

FIG. 3 shows a simple artificial leg arrangement 30, wherein an upper leg member 31 terminates with a stump element 32, which is pivotally connected to a lower leg member 34 by means of joint 33. A main body 36 of a hydraulic damper 35, having a main body 36, is connected with the lower leg 34 at coupling point 37, which coupling point 37 allows relative movement therebetween. A member 38 of the hydraulic damper 35 associated with a piston and arranged for reciprocating motion with respect to the main body 36 is connected to the stump element 32 at coupling point 39 and is similarly arranged for movement, in this case, relative to the stump element 32. Whilst the following description describes the hydraulic damper in relation to a lower leg prosthesis, it is to be understood that the hydraulic damper can be utilized in relation to other prosthetic orthopedic skeletal joints, for example a hip to an upper leg joint, an upper arm to a shoulder, etc.

One general issue associated with mechanical joints is that the response of the joint controller is dependent upon a load applied and not necessarily to a kinematic requirement that commands a movement pattern independent of load as possible. This means that a correct and safely maintained response is required in each of the two alternating operating states of a prosthetic; namely, a low reactive torque state, such as typically in a swing phase, and a state of high reactive torque under weight bearing. An inappropriate torque level typically means a severe disruption of gait. The present invention addresses this and provides an adaptive degree of resistance to flow—whether in stumble recovery or in a change of gait.

Referring now to FIG. 4, there is shown a simplified view of a hydraulic damper unit prior to placement of a control element in accordance with the present invention. Hydraulic damper unit 35 comprises a hydraulic arm element 38 which is coupled to an artificial leg part 32 by connection 39 at an end opposite to that of a main body 36 and by connection 37 at an end opposite to that of hydraulic arm element 37 with artificial leg part 34. Hydraulic arm element 38 comprises a piston 43, which moves relative to bore 44 to define a variable volume chamber 42. Hydraulic fluid from the variable volume chamber 42 is operable to pass to valve 47 into an accumulator 40 via fluid path 45, 47c. Indeed, in some embodiments, the valve assembly could comprise part of the piston assembly. In use, as the piston approaches valve 47, fluid is caused to go through the valve; the rate of flow of fluid is controlled by the valve; since the valve reduces the flow rate under high pressure, then the movement of the damper is conditioned to be gradual. However, upon withdrawal of the piston, away from the valve, then one-way valve 46 can allow free and unhampered return flow of hydraulic fluid from the accumulator to the variable volume chamber 42. Element indicated by reference numeral 48 serves to raise the seat 47a of valve 47 from a mutually facing valve seat 47b. Flow path 47c leads from valve 47 towards accumulator 40. As will be appreciated, the space 40a (which is at the same pressure as in the accumulator) between the valve seat, at the base of the element 48, and the base of the bore will be filled as the pressure within the valve area urges the valve 47 towards the piston, whereby further descent of the piston 43 will maintain fluid flow.

In this example, the hydraulic damper is fitted to a leg prosthesis, with limb element 32 comprising an upper leg element, limb element 34 comprising a lower leg limb and the joint 33 being the knee. The knee will operate over an angular range, typically, of 120°. In ambulatory mode, the lower leg will extend forwardly and flex rearwardly. Accordingly in flexion mode (indicated by arrow denoted FL) the piston 43 will approach the valve in compression, reducing the volume of the variable volume chamber 42, causing fluid flow through the valve 47, conditional upon the valve seat faces 47a and 47b being separated. The valve faces can only be separated if prior to the separation the widened top portion of element 48 has been raised by the reduced width or neck section of the piston by a degree of overextension of the knee joint that effectively causes movement of piston 43 within cylinder bore 44 defined in body 36, away from valve seat 47b. On immediate flexion effort, and after this brief event, fluid flow is still possible through valve seat 47a, 47b and, which in turn, immediately builds up a pressure between 47a and 47b, due to a flow resistance arising through gate 47c. As long as flexion continues, fluid flow through area 47c will continue, maintaining the pressure that is conditioning valve seat 47a to remain separate from valve seat 47b, thereby permitting fluid flow through the valve. The pressure in the vicinity of valve seat 47c will maintain this state because the opposing pressure in volume 40a is not greater than the reference pressure in accumulator 40. If the hyperextension does not happen and the piston is pressed straightaway, then auxiliary valve 47d will operate in default and shall allow limited movement, allowing fluid transfer from the variable volume chamber through to the accumulator albeit at a reduced rate; the pressure in volume 42 ensuring maintenance of fluid pressure on body 48 causing valve 47 to remain closed.

In contrast, in extension mode, with movement in direction corresponding to arrow EL, the pressure in valve 42 is lower than in the accumulator, which will mean the gap 40a is increased to a maximum as the accumulator fluid acts in the area of this gap. Simultaneously, the one way valve 46 will open allowing the accumulator fluid to enter into the variable volume chamber 42, causing extension of the hydraulic arm 38 as the piston 43 is caused to withdraw from the valve 47.

The force of the hydraulic pressure induced by the flow within the variable volume chamber is transmitted (in certain embodiments, for example see example valve per FIG. 4d) by connecting rod 48 to the valve, whereby operation of the valve is directly controlled by such hydraulic pressure. In such arrangements, an outlet aperture of the valve reduces in size; In the examples hydraulic pressure acting on the valve causes an aperture to be physically occluded, as will be discussed in further detail to the specific valve mechanisms below, whereby to reduce the flow of fluid from the variable volume chamber, with the result that movement of the piston within the bore is reduced and so any movement is effectively "damped".

It is to be understood that when valve 47a-47b is almost—but not fully—closed, spring 47e will provide a force to close the said valve 47a-47b. However, a flow through the valve is present and builds a pressure level in front of gate 47c, which said pressure as a function of the flow conditions the valve 47a to be lifted against spring tension 47e. When the driving pressure of variable volume chamber 42 increases a little, the valve seat portion 47a is raised a little more and a variable aperture between valve seats 47a and 47b increases in size, reducing the pressure drop across it. The lift in valve portion 47a is also associated with an increase in axial force 47e arising from a resilient member (not indicated) and more pressure is required to cause further valve lift. Advantageously the valve can be made to have the fluid flow condition the dynamic state of the aperture. FIG. (4a) shows a response rate typical for this arrangement.

The advantage of the flow conditioned performance of the disclosure is found in the possibility to have a valve that permits a swing movement in the knee, but also allows a gradual closure of the valve on termination of the initial knee flexion movement, so that the valve does not abruptly close and smoothly completes the termination of movement in knee flexion, which provides comfort and quality in proprioceptive feedback to the user. In accordance with the present invention, a system as is known where the flow rate of a hydraulic fluid within a hydraulic damper as it flows back and forth between first and second reservoirs between a valve is provided with a sensor whereby the rate of flow can be monitored so as to adapt a valve functionality; to increase the resistance in a stumble recovery mode for a prosthetic leg; to reduce the resistance as the speed of a continuous gait increases. The sensor can conveniently be arranged as a vane which moves in accordance with the direction of flow of fluid between the first and second reservoirs and, for example, becomes increasingly deflected the greater the speed of flow of fluid. In a first alternative a rotary paddle could be employed, such that the rotation of the paddle is measure of the degree of rate of change of fluid flow rate.

In the event that the flow stops instantaneously, then a stumble recover mode could be instigated, causing fluid flow through a valve to be minimized or even prevented: instead of maintaining the valve in a controlled open state by preventing valve closure by magnetic force, a field reversal would instead force rapid valve closure. Such a stumble recovery mode could be determined with reference, for example, to the degree of extension of a hydraulic rain within a cylinder of the hydraulic damper, to ensure that a no-flow operating condition is not instigated when no benefit would be realized. The vane could be connected to a microprocessor to determine when valve operation needs to be varied from a quiescent state. In the event that a rotary paddle assembly is employed, the rotation and rate of change of rotation could be determined with reference to rotary position indicia. In the alternative a de voltage could be generated which is either employed directly to control a valve control mechanism or, is amplified by an electrical amplification circuit, when a power supply would also be required. The electricity output from a small generator is conveniently damped and stored using capacitors; either directly or with amplified power, an electromagnet or other electro-positioning unit can be employed to alter the operating characteristics of a valve; from being fully closed in a stumble recovery mode to a condition of providing less resistance when an increase in gait is desired, the valve acting between two chambers of a damper can be further, additionally controlled. The valve can comprise a moveable element which abuts a resiliently mounted element which reduces the size of an aperture as the force increases and acts against the resiliently mounted element the degree of resilience being varied, for example by a varying magnetic field, controlled by the operation of the sensors. A rheomagnetic fluid can be employed, whereby a magnetic field can determine the flow characteristics of the hydraulic fluid to be continuously controlled by a variable electromagnet under control of a microprocessor.

Referring now to FIG. 4', there is shown a valve control element in accordance with the present invention. Housing body 11 contains a cap 4. Hydraulic fluid flow 5 occurs through orifice 12, which then passes through the valve and through orifice 10 in a direction indicated by reference numeral 3. The hydraulic fluid flow through 5 also causes the external pressure at 6, which is partially counter balanced by internal pressure 7. As pressure 6 is greater than 7 cap 4 moves downwards blocking exit hole 10. There is a pressure drop to low pressure region 9, causing the hydraulic fluid to flow from the high pressure to the low pressure region. This will naturally diminish outward flow 3, and therefore inward flow 5. There will be equilibrium where 10 is partially closed, if there is a resistive force acting upwards compensating for the pressure difference across orifice 12. This force, in accordance with the present invention, is controllably variable by altering the current 13 flowing through coil 2. This causes the electromagnetic field lines to interfere with permanent magnet 1, to cause a repelling action 8 and this will bring a change in the upward force. By altering the current, cap 4 can move upwards, and hence can control the degree of opening of the valve 10. A balance between the orifice 10 closing force from the difference between pressures 6 and 7 is determined, a natural function of flow through orifice 12, which is distinct to the quiescent condition (in the absence of the present invention) and repelling forces from magnet 1 and coil 2, and this balance is variable by current 13. Indeed if current 13 were to be reversed, this valve would instantly change to a closed condition as port 10 would be closed and block all flow 3.

Indeed this construction can be the basis for many alternative embodiments: an electro magnet may repel a permanent magnet, or in an alternative embodiment may attract a permanent magnet. Alternatively an electromagnet coil may be placed in association with the moveable skirt and act on a static magnet by means of repelling or attraction. In an alternative, the magnet can comprise an electromagnet, and the device can be built with solenoids in attraction or by means of repelling, a simple solenoid can act on a ferromagnetic material to cause a controlling force to act upon the moveable element. Such magnetic forces can be applied instead of the forces arising from known resilient members. Alternatively, the magnetic forces can be applied as modifiers to a base level force supplied by such known resilient members. In other words the magnetic field forced may be employed to enhance the force of the resilient member, and therein typically enhance the flow through the valve, or the magnetic force may assist the pressure drop across the inlet orifice and therefor reduce the valve through flow, all controlled by the instant level of current through the coils. As will be appreciated, the total replacement of such resilient members by the electromagnetic forces would require more current but would add a greater degree of control to flow through the valve. The basic property of the valve controlling flow by a control force has a useful advantage over stepper motors as found and used in other prior art, especially since response time of the disclosure is in milliseconds as opposed to tenths of seconds.

In prior systems, it has been suggested that a magnetic coil can be used as a control element; a repelling force can be used as drawn in FIG. 4', but equally can be used to lift the same valve control element 4 if placed above. The effective difference is naturally found in the relationship between force and displacement. If the construction uses a repelling force, the force reduces on opening the exit aperture 10 due to displacement, but if the force is used in an attractive sense (when the coil is placed on the top side) then the attraction force will become stronger, as the distance between the permanent magnet and the coil reduces. Although the small range of travel to control port 10 may appear to be of little consequence, such subtle differences will have greater effect in prostheses for children and diminutive statured adults. Effectively, the provision of an electro-magnetic (or otherwise) control element to a conditional flow valve to stabilize flow largely independent of pressure difference across the whole of the valve by means of a force generated by a current that by its nature can instantly cause total valve closure on withdrawal and or reversal of current can provide enhanced benefits. For example, the present invention can provide a valve closure system can be of benefit in the case of a 'stumble recovery' mode that is necessary for a safe and normal mode of operation for an amputee. Stumble recovery is necessary in the following circumstance: an amputee swings a limb forwardly and in so doing stubs a toe on the ground whereby further limb extension is inhibited. In such a situation, however, forward momentum of body and trunk cannot be stopped and so the other limb ought to be brought forward urgently. That is to say, an artificial limb in accordance with the present invention can provide the required degree of stability and stiffness, by closing the valve, thereby preventing flow of fluid through the valve. It is noted that the prior art resilient member cannot provide this advantage, since the resilient member, or biasing element inherently prevents the valve from closing, and in fact only limits the flow to a predetermined maximum, whereas in stumble recovery this flow should be zero. This disclosure demonstrates how fluidic technology can be used as an actuator in electro-technical control, or microprocessor control.

Referring now to FIG. 4a, an example valve 47a is shown having an inlet 471a set within a movable cap 472a having a cylindrical skirt 473a which is fitted for resilient movement within a bore defined in a base member 474a, which cap is closely fitting within the bore; a spring biasing element 475 urges the cap away from the inside of the base member 474a, movement of the cap being delimited by an abutment means (not shown). Cap 472a has an aperture 474a which provides an opening to a fluid flow path within the base member to exit aperture 476a. When an increase in hydraulic pressure exists relative to an exit volume (the accumulator pressure) then the cap is urged against the force of the biasing element and moves inwardly toward the base member, whereby the skirt 473a occludes the exit aperture 476a.

Referring now to FIG. 4b, an example valve 47b is shown having an inlet 471b defined between the lips 470b of a base member 474b. A movable cap susceptible to pressure control rod 48, for example, comprises a resilient disc spring 475b. As will be appreciated in quiescent state, spring biasing element 475b urges the cap away from the inside of the base member 474b. When an increase in hydraulic pressure exists relative to an exit volume (the accumulator pressure) then the cap is urged against the force of the biasing element and moves inwardly toward the base member, whereby the biasing element retracts toward the base member occluding exit aperture 476b.

Referring now to FIG. 4c, an example valve 47c is shown having a movable cap 472c having a cylindrical skirt 473c. An inlet 471c is defined within the skirt 473c of the cap. The cap 472c is adapted for resilient movement within a bore defined in a base member 474c, which cap is closely fitting within the bore; a spring biasing element 475 urges the cap away from the inside of the base member 474c, movement of the cap being delimited by an abutment means (not shown). Cap 472c has an aperture 471c, which provides an opening to a fluid flow path within the base member to exit aperture 476c. When an increase in hydraulic pressure exists relative to an exit volume (the accumulator pressure) then the cap is urged against the force of the biasing element and moves inwardly toward the base member, whereby to partially occlude the inlet aperture 471c; as is the case with FIG. 4a, the skirt 473a also occludes the exit aperture 476c.

FIG. 4d shows a still further variant: valve 47d is shown having a movable cap 472d having a cylindrical skirt 473d. An inlet 471d is defined within a closed end of the cap, which is also mechanically connected to the piston 43, per FIG. 4. The cap 472d is adapted for resilient movement within a bore defined in a base member 474d, which cap is closely fitting within the bore; a spring biasing element 475 urges the cap away from the inside of the base member 474d, movement of the cap being delimited by an abutment means (not shown). Cap 472d has an aperture 471d which provides an opening to a fluid flow path within the base member to exit aperture 476d. When an increase in hydraulic pressure exists relative to an exit volume (the accumulator pressure) then the cap is urged against the force of the biasing element and moves inwardly toward the base member, whereby to partially occlude the exit aperture 476d.

FIG. 4e shows a still further variant, although this valve is useful where movement is required when the valve is in a particular orientation in space and may be placed in parallel with another valve or in a parallel fluid circuit. The system includes all the features of valve 47a—features of the cap 474a and 474e correspond, as do the base members 474a and 474e, skirts 473a and 473e and exit apertures 476a and 476e. However pendulum element 477, equipped with a sealing weight member 478, is operable to move when displaced from the vertical and can provide fluid passage with respect to corresponding pendulum valve seat face 479 when not in a vertical orientation. It will be appreciated that a number of these valves can be utilized in groups or on their own. The biasing element can be changed to provide different levels of resilience. Equally, the resilient element is ideally placed upon an adjustable seat member with the base, whereby to enable adjustment, either on build, or conveniently for fine adjustments, once the damper has been fitted within a prosthetic device and an amputee is utilizing the device.

Accordingly, in one aspect of the invention, there is provided a pressure sensitive valve wherein inlet fluid is caused to circulate about a central aperture, Upon attainment of an appropriate flow rate through the vortex valve, a void is induced. The creation of a void, which is believed to comprise hydraulic oil vapors, effectively reduces the aperture dimensions, thus restricting flow, In turn, the flow of fluid from. the variable volume chamber is reduced, with the result that movement of the piston within the bore is reduced and so any movement is effectively "damped", it will be appreciated that this valve can have many applications associated with fluid control of prosthetics, not just the specific application with which reference has made. It will be appreciated to those skilled in the art that this type of fluid control can be used in ankle joints and other types of joints in sensory control.

Figure 5A:
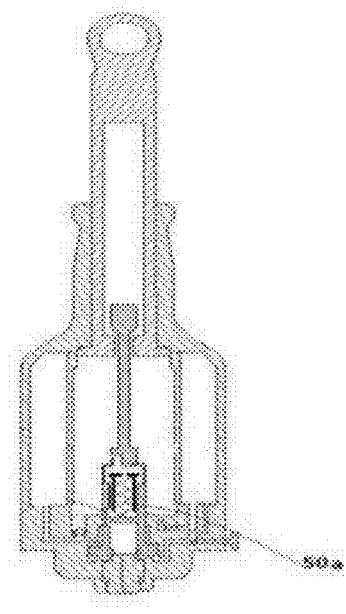
Figure 5C:
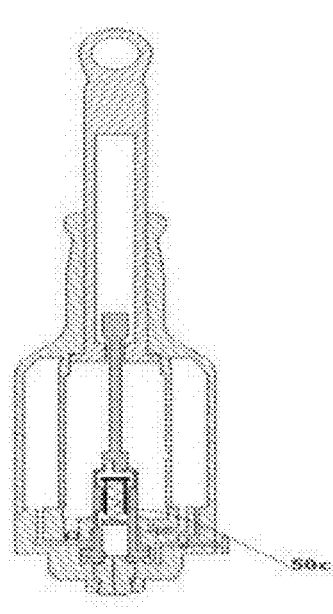
Figure 5D:
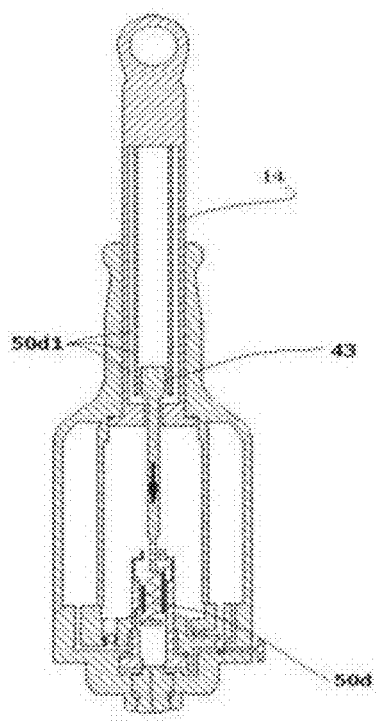
Figure 5B:
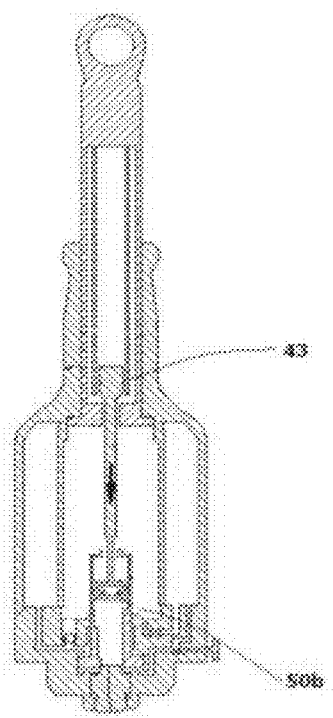

Referring now to FIGS. 5a-5e, there are shown a number of variants, which will be selected to provide suitable responses and operating characteristics for particular patients, amputees etc., when fitted with variants of the present invention. FIG. 5a shows in situ a simple embodiment of the valve with a simple metering aperture 50a and the resilient spring has a constant spring rate in its duty range corresponding to the valve described in with reference to FIG. 4a. This can be utilized in a hip joint or ankle joint where uniformity of response is required. FIG. 5b is an embodiment provided with a gravity sensitive variable metering aperture 50b and shows a valve corresponding to the valve described in with reference to FIG. 4b.

FIG. 5c is appropriate for geriatric knee joints where, as a leg is lifted off the ground, and only then is swung rearwardly, the inertia of the foot assembly is typically insufficient to cause a complete closure of the valve 47 and a stepped horizontal force-flexion curve is followed if the patient attempts to collapse on the knee joint whilst: the weight of the patient is sufficient to cause an increase in pressure to cause final closure of the metering aperture 50c. This valve corresponds to fitment of valve 4c.

Figure 5E:
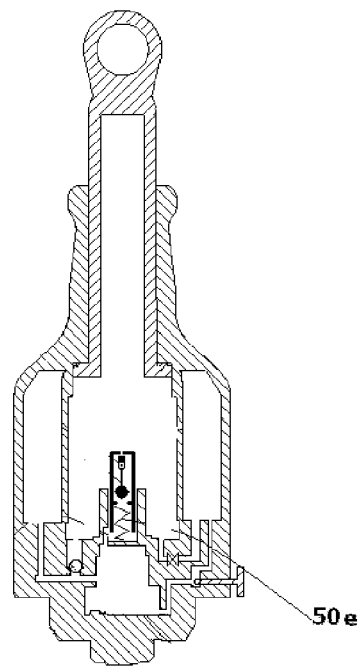

FIG. 5d shows a still further embodiment, wherein the force applied to the valve is conditional upon the extent of insertion of the piston within the bore as well as the force being applied to the hydraulic arm 37. This is enabled by the use of tube 50d1, within which the pressure sensing head 43 associated with the pressure feedback device can move; by use of various holes, a change in response pressure with respect to piston travel can be enabled. The holes can vary in shape i.e. become narrower toward the coupling end of the hydraulic arm, or vice versa. FIG. 5e shows a further embodiment wherein the valve mechanism comprises a resilient disc, which covers a correspondingly dimensioned aperture. Since the disc, in operation, closes over the valve, the flow, in the limit will be laminar, serving to provide a smooth response. A lower build height can also be achieved, which is of particular advantage in small joint prostheses, such as ankles and in prostheses for children.

The present invention' can thus easily and simply have pre-determined response curves which vary in either force or piston distance (or both). A response curve can be created to provide a correct kinematic response tailored for a particular patient.

FIG. 6 is a graph that represents the maximum knee flexion angle in swing at various walking speeds for an amputee walking with the aid of the present invention. The graph shows a minimal change in angular variation of knee flexion movement with respect to an increase in walking speed. The plot of knee flexion for a normal gait, i.e. for a person with the full use of their own limbs is shown for comparative purposes. It can be seen that the variation in knee flexion angle is more or less absent, for both the amputee and a control person, with full use of their own legs, despite an increase in speed to approximately double that of the initial speed. In simple terms, to the casual observer, the person wearing such artificial limbs would be seen to have an ungainly gait due to a delay in knee extension needed to prepare the limb for weight acceptance.

Problems arising from the use of weight activated knee joint control mechanisms include the fact that the residual weight taken by an artificial limb on toe off can interfere with the walk and the knee flexion range is adjusted to 65°-70°, as opposed to a natural knee flexion range of 55°-60°. The knee flexion range can be adjusted to correspond closely with the knee flexion range of a natural leg, but this has been found not to be as beneficial as with the case of a slight increase in knee flexion range. It is to taken into account that the prosthetic leg and foot cannot provide feedback signals to the user of the leg relating to proximity to the ground and other objects upon or close to the ground and it has been found that the simple expedient of ensuring a slightly greater range of knee flexion reduces a risk of grounding the foot in normal use.

FIGS. 7, 8 and 9 conveniently show variants of the invention that can easily and simply he realized by the man skilled in the art. In these figures, inlet aperture 821 allows fluid to flow from a higher-pressure region 831 to flow through variable size exit aperture 827 to flow to downstream lower pressure 828, Flow through aperture 821 causes a pressure drop across cross sectional area of body 822 that has means move up or down to operate size 827. The pressure drop across cross sectional area of 822 causes a force F that must overcome force generated by:

In FIG. 7 a piezoelectric element 826, is shown, where deformation pivotably amplified over fulcrum 830 and by beam 829 to resist force F to close exit 827 . The balance of forces determines the flow through put: if F becomes too great due to increased flow, exit 827 causes more restriction to flow, increasing back pressure in 837 , decreasing pressure drop across cross sectional area of 822, limiting closing of 827 , stabilizing flow, the piezoelectric voltage being provided by wires 825 and 824.

In FIG. 8 a repulsive electrostatic field 834 creates a field acting on plates 823 (stationary), plate 833 connected to moveable body 822 resists force F to close exit 827. The balance of forces determines the flow through put: if F becomes too great due to increased flow, exit 827 causes more restriction to flow, increasing back pressure in 837, decreasing pressure drop across cross sectional area of 822, limiting closing of 827, stabilizing flow, the electrostatic voltage being provided by wires 825 and 824.

In FIG. 9 a repulsive magnetic field 839 arising by current flow through coil 835 and permanent magnet 840 fixed to body 822 (or alternatively, another but opposing electromagnet) resist force F to close exit 827. The balance of forces determines the flow through put: if F becomes too great due to increased flow, exit 827 causes more restriction to flow, increasing back pressure in 837, decreasing pressure drop across cross sectional area of 822, limiting closing of 827, stabilizing flow, the electrical input voltage being provided by wires 825 and 824.

The present invention enables adaptive movement control operating mechanism effectively independent of the pivot mechanism. That is to say, many pivot mechanisms such as knee designs can be monocentric, where there is a single pivot of the gross motion of the artificial limb, whilst there are also several designs are so called polycentric, where a number of linkages cooperate to provide a complex gross motion. Whether the total motion of the knee joint is complex or simple, the stability still needs to be assured, and any swing phase needs to be controlled and a damper in accordance with the present invention can provide significant benefit.

The skilled person will be aware of a range of possible modifications of the various embodiments described above. Accordingly, the present invention is defined by the claims and their equivalents.

What is claimed is:

1. A prosthesis comprising a first artificial limb component, a second artificial limb component, a joint pivotally coupling said first and second limb components to permit extension and flexion movements about the joint and a hydraulic damper comprising a variable volume chamber for hydraulic fluid coupled between said first and second limb components, wherein the damper is operable to allow relative movement of said first and second limb components about the joint by passage of an incompressible hydraulic fluid through said variable volume chamber via an aperture of a valve, the valve being operable to determine a degree to which the hydraulic damper reactively resists a force to permit movement by a first pressure, which first pressure acts on a wall of the variable volume chamber;

wherein the valve is disposed between the variable volume chamber and a hydraulic fluid sink on a second side of the valve;

wherein a fluid flow rate of the incompressible hydraulic fluid through the valve is a conditioned function of a second pressure, which second pressure is less than the first pressure and is associated with fluid flow through the valve and is operable to maintain a positive flow rate through the valve as the first pressure increases, the conditioned function being determined such that the second pressure as a function of the flow rate causes an increase in resistance of the valve to the flow caused by the first pressure, such that the fluid flow approaches but does not reach a maximum as the first pressure increases past a minimum pressure, whereby a fluid flow limit is established through the valve; and wherein a sensor is provided that is sensitive to the rate of flow of fluid passing from the variable volume chamber to the hydraulic fluid sink and vice versa, whereby to provide piezoelectric, magnetic, electro-magnet and/or electrical signals to enable control of a moveable body which acts upon the valve to enable an increase or decrease of flow of hydraulic fluid through the valve.

2. The prosthesis of claim 1, wherein the feedback signals from the sensor enable an electromagnetic element to operate and to control the operating characteristics of the valve.

3. The prosthesis of claim 1, wherein the feedback signals from the sensor enable an electromagnetic element to operate and to control the operating characteristics of the valve and wherein the feedback signals from the sensor control the operating characteristics of the electro-magnet, to change an electro-magnetic field acting upon a moveable member of the valve can provide additional flow restriction, to provide valve closure relative to an input signal, whereby the magnetic force can restrain valve closure to provide the said fluid flow limit in accordance to the electric current causing the electromagnetic field, and whereby the electro-magnetic field can be instantly be varied or reversed to provide a fully controllable response of the valve to pressure and flow.

4. The prosthesis of claim 1, wherein the feedback signals from the sensor enable a magnetic element to operate and to control the operating characteristics of the valve.

5. The prosthesis of claim 1, wherein the feedback signals from the sensor enable a piezoelectric element to operate and to control the operating characteristics of the valve.

6. The prosthesis of claim 1, wherein the fluid is a rheomagnetic fluid, whereby a magnetic field can determine the flow characteristics of the hydraulic fluid to be continuously controlled by a variable electromagnet under control of a microprocessor.

7. A prosthesis according to claim 1, wherein, in the absence of control by means of said sensor, the effective size of the aperture is a function of the head loss arising from a proportion of the fluid flow through a metering conduit, the resultant head loss acting upon a moveable element against resistance of a resilient element to vary the effective aperture size.

8. A prosthesis according to claim 1, wherein, in the absence of control by means of said sensor, the effective size of the aperture is a function of the head loss arising from a proportion of the fluid flow through a metering conduit, the resultant head loss acting upon a moveable element against resistance of a resilient element to vary the effective aperture size, and wherein the force created to overcome the said resistance is further conditioned by a relative state of the hydraulic damper and the degree of extension/flexion of the limb elements.

9. A prosthesis according to claim 1, wherein the effective aperture is determined by at least one of an inlet aperture and an outlet aperture of the valve.

10. A prosthesis according to claim 1, wherein, in the absence of control by means of said sensor, the effective size of the aperture is a function of the head loss arising from a proportion of the fluid flow through a metering conduit, the resultant head loss acting upon a moveable element against resistance of a resilient element to vary the effective aperture size and wherein the resistance to said flow by said metering conduit is further conditioned by the position of the moveable element.

11. A prosthesis according to claim 1, wherein the effective aperture is determined by at least one of an inlet aperture and an outlet aperture of the valve and wherein the resistance to said flow by said effective aperture is further conditioned by the position of the moveable body.

12. A prosthesis according to claim 1, wherein, in the absence of control by means of said sensor, the effective size of the aperture is a function of the head loss arising from a proportion of the fluid flow through a metering conduit, the resultant head loss acting upon a moveable element against resistance of a resilient element to vary the effective aperture size and wherein the resistance to said flow by said metering conduit is further conditioned by the position of a gravity sensitive element.

13. A prosthesis according to claim 1, wherein the effective aperture is determined by at least one of an inlet aperture and an outlet aperture of the valve and wherein the resistance to said flow by said effective aperture is further conditioned by the position of a gravity sensitive element.

14. A prosthesis according to claim 1, wherein, in the absence of control by means of said sensor, the effective size of the aperture is a function of the head loss arising from a proportion of the fluid flow through a metering conduit, the resultant head loss acting upon a moveable element against resistance of a resilient element to vary the effective aperture size and wherein the resistance to said flow by said metering conduit is further conditioned according to the relative position of said first and second limb components.

15. A prosthesis according to claim 1, wherein the effective aperture is determined by at least one of an inlet aperture and an outlet aperture of the valve and wherein the resistance to said flow by said effective aperture metering conduit is further conditioned according to the relative position of said first and second limb components.

16. A prosthesis according to claim 1, wherein, in the absence of control by means of said sensor, the effective size of the aperture is a function of the head loss arising from a proportion of the fluid flow through a metering conduit, the resultant head loss acting upon a moveable element against resistance of a resilient element to vary the effective aperture size and wherein the variable aperture is created by a surface of the resilient element occluding the aperture according to its proximity and resilience.

17. A prosthesis according to claim 1, wherein the effective aperture is determined by at least one of an inlet aperture and an outlet aperture of the valve and wherein the variable aperture is created by a surface of a resilient element occluding the aperture according to its proximity and resilience.

18. A prosthesis according to claim 1, wherein, in the absence of control by means of said sensor, the effective size of the aperture is a function of the head loss arising from a proportion of the fluid flow through a metering conduit, the resultant head loss acting upon a moveable element against resistance of a resilient element to vary the effective aperture size and wherein the variable aperture is created by the movable body occluding the aperture according to the deflection of the resilient element.

19. A prosthesis according to claim 1, wherein the effective aperture is determined by at least one of an inlet aperture and an outlet aperture of the valve and wherein the variable aperture is created by the movable body occluding the aperture according to the deflection of a resilient element.

* * * * *